United States Patent [19]

Stieber

[11] Patent Number: 4,631,316
[45] Date of Patent: Dec. 23, 1986

[54] CURABLE RUBBER COMPOSITIONS COMPRISING SUBSTITUTED DITHIOCARBAMYLUREA ACCELERATORS

[75] Inventor: Joseph F. Stieber, Prospect, Conn.

[73] Assignee: Uniroyal Chemical Company, Inc., Middlebury, Conn.

[21] Appl. No.: 585,072

[22] Filed: Mar. 1, 1984

[51] Int. Cl.$^4$ ............................................. C08C 19/20
[52] U.S. Cl. ..................................... 525/352; 525/348; 525/349
[58] Field of Search ............... 525/331.8, 332.6, 333.1, 525/352, 348, 349

[56] References Cited

U.S. PATENT DOCUMENTS 3,546,185  12/1970  Coran .................................. 525/352
4,268,640  5/1981  Matoba ............................... 525/352

Primary Examiner—Christopher Henderson
Attorney, Agent, or Firm—William E. Dickheiser

[57] ABSTRACT

A compound of the formula $$R^1—NHC(O)NHSC(S)NR^2R^3$$

wherein $R^1$ is phenyl; phenyl substituted with halogen, alkyl, $NR^4R^5$ wherein $R^4$ and $R^5$ are the same or different and are hydrogen or alkyl; alkoxy, alkylthio, methylenedioxy, $COOR^6$ wherein $R^6$ is alkyl; or NHCOOR wherein $R^7$ is alkyl; $R^2$ and $R^3$ are the same or different and are alkyl, cycloalkyl or aralkyl, and $R^2$ plus $R^3$ are alkylene, oxydialkylene or thiodialkylene.

1 Claim, No Drawings

CURABLE RUBBER COMPOSITIONS COMPRISING SUBSTITUTED DITHIOCARBAMYLUREA ACCELERATORS

BACKGROUND OF THE INVENTION

1. Field of the Invention

This invention relates to novel dithiocarbamylureas which are useful as rubber curing agents.

2. Reference of Interest

U.S. Pat. No. 3,947,511, discloses compounds having the structure $X(NHC(O)NRSC(S)NR^1R^2)_n$, wherein R and $R^1$ may be the same or different and are hydrogen, alkyl, cycloalkyl, aralkyl, etc.; $R^2$ may be alkyl, cycloalkyl, aralkyl, etc.; $R^1$ and $R^2$ together may be polymethylene or oxydiethylene, n may be 1 or 2, and if n equals 1, X is $C_1$-$C_8$ alkyl. If n equals 2, X is alkylene, O— or S interrupted alkylene, alkenylene, alkylenbis(arylene), arylenebis(alkylene), or aryl of up to 13 carbon atoms. A compound typical of the U.S. Pat. No. 3,947,511 is $C_2H_5NCH(O)NHSC(S)-N(CH_3)_2$.

It has been found that the urea accelerators of the instant invention exhibit superior performance over the closest known prior art.

Compounds of the instant invention may be employed as rubber curatives, usually in combination with sulfur and optionally with other rubber curing agents such as mercaptobenzothiazole disulfide, N,N-oxydiethylenebenzothiazolesulfenamide and the like. Rubbers which can be cured with the instant compounds include natural rubber, cis- or trans-polyisoprene, polybutadiene, styrene-butadiene copolymer, acrylonitrile-butadiene copolymer, ethylene-propylene-non-conjugated diene terpolymer and the like.

DESCRIPTION OF THE INVENTION

The compounds of this invention are prepared by the reaction of an S-(dialkylthiocarbamyl)sulfenamide with the appropriate aromatic isocyanate. The reaction is usually done by reacting the two components in a solvent.

Solvents suitable for use in the invention are aliphatic and aromatic hydrocarbons such as hexane, isooctane, benzene, toluene, and xylene, and their halogenated derivatives as chloroform, carbon tetrachloride, 1,1,1-trichloroethane, trichlorotrifluoroethane, and chlorobenzene or ethers. The reactants can also be contacted in melt form if desired. In large-scale preparations, however, the use of an inert solvent is advantageous to aid in control of the reaction.

For most effective utilization of materials, the reactants are usually mixed together in molar equivalents.

The reaction is conveniently carried out at temperatures of 10° to 130° C., preferably 25° to 110° C., most preferably 70°-90° C. Pressure is not critical, and ambient pressure is usually used for the sake of convenience.

The reaction proceeds in the presence or absence of catalysts. Catalysts are advantageous in enabling the use of lower temperatures and/or shorter times. The alkyltin dialkanoates, such as dibutyltin dilaurate, are suitable. Tertiary amines such as trimethylamine, triethylamine, tripropylamine, tetramethylethylenediamine, 1,4-diazabicyclo[2.2.2]octane, and pyridine are also effective catalysts.

The products are recovered by known means, such as filtration from the reaction solvent as they crystallize out, or by evaporation of the reaction solvent. The products may be purified if desired by recrystallization from known organic solvents.

The compounds of the invention have the formula $$R^1—NHC(O)NHSC(S)NR^2R^3$$

wherein $R^1$ is phenyl; phenyl substituted with halogen, $C_1$-$C_{12}$ alkyl, $NR^4R^5$ wherein $R^4$ and $R^5$ are the same or different and are H, $C_1$-$C_6$ alkyl; $C_1$-$C_8$ alkoxy, alkylthio, methylenedioxy, $COOR^6$ wherein $R^6$, is $C_1$-$C_{12}$ alkyl; or $NHCOOR^7$ wherein $R^7$ is $C_1$-$C_8$ alkyl; $R^2$ and $R^3$ are the same or different and are $C_1$-$C_{18}$ alkyl, $C_5$-$C_6$ cycloalkyl or $C_7$-$C_9$ aralkyl, and $R^2$ plus $R^3$ are $C_4$-$C_6$ alkylene, $C_3$-$C_4$ oxydialkylene or thiodialkylene.

Preferably $R^1$ is phenyl; phenyl substituted with Cl, Br, $C_1$-$C_4$ alkyl, $NH_2$, $C_1$-$C_4$ alkoxy, $C_1$-$C_4$ alkylthio, $COOR^6$ wherein $R^6$ is $C_1$-$C_2$ alkyl or $NHCOOR^7$ wherein $R^7$ is $C_1$-$C_2$ alkyl.

$R^2$ and $R^3$ are the same or different and are $C_1$-$C_{12}$ alkyl, $C_5$-$C_6$ cycloalkyl or benzyl.

$R^2$ plus $R^3$ are tetramethylene, pentamethylene, oxydiethylene or thiodiethylene.

Most preferably $R^1$ is phenyl or phenyl substituted with Cl, $CH_3$, $CH_3O$, $CH_3S$, or $NHCOOCH_3$.

$R^2$ and $R^3$ are the same and are $C_1$-$C_4$ alkyl, cyclohexyl, oxydiethylene or benzyl.

Thus, a sulfenamide having the formula $H_2NSC(S)NR^2R^3$ is reacted with isocyanate having the formula $R^1(NCO)_n$; wherein $R^1$, $R^2$ and $R^3$ have the meanings above and n is 1 or 2. It should be noted that if n is 2, the reaction between the sulfenamide and the diisocyanate is carried out at or below 80° C., and subsequently the remaining isocyanate groups are contacted with the appropriate alcohol to hield the compound of this invention wherein $R^1$ is phenyl substituted with the respective $NHCOOR^7$ group.

It has been found that compounds of the instant invention provide improved scorch safety at processing temperatures and/or faster cure rates at cure temperatures. Rubber treated with compounds of this invention also have improved physical characteristics, especially in regard to elongation.

The following examples illustrate specific embodiments of the invention without necessarily limiting the scope of the invention:

EXAMPLE 1

N,N-Dimethylthiocarbamylthio-N'-phenylurea (Compound No. 1)

Phenylisocyanate (23.8 g, 0.20 mole) and dibutyltin di-2-ethylhexanoate (0.40 g) were added to a solution of S-(dimethylthiocarbamyl)sulfenamide (27.2 g, 0.20 mole) in toluene (400 ml). The mixture was heated to 85°-95° C. on a steam bath and stirred for 2.5 hours. Then the hot slurry was filtered and the isolated product was dried in a 60° C. oven. Yield: 42.8 g, 83.9% mp 185°-188° C. The product was washed with hot tetrahydrofuran and dried. mp 193°-194° C.

EXAMPLE 2

N-Dimethylthiocarbamylthio-N'-(3-methoxycarbonylamino-4-methylphenyl)urea (Compound No. 7)

Toluene-2,4-diisocyanate (17.9 g, 0.10 mole) and dibutyltin di-2-ethylhexanoate (0.20 g) were dissolved in toluene (100 ml). The solution was heated to 75° C., and then a solution of S-(di-methylthiocarbamyl)sulfenamide (13.6 g, 0.10 mole) in toluene (200 ml) was added slowly, with constant stirring, over a period of 45 minutes. When the addition was complete, the mixture was maintained at 70°–80° C. and stirred for an additional hour. Then anhydrous methanol (15 ml) was added. The slurry was stirred and maintained at 70°–80° C. for one more hour. The slurry was cooled to room temperature and filtered. The white powdery product was dried at 60° C. Yield 30.5 g, 89.2%, mp 180°–185° C. IR and NMR spectra were consistent with the assigned structure.

Compounds 2–6 were made essentially according to the above procedures. All such compounds are summarized in Table I as well as additional chemicals (8–14) which can be prepared and used within the scope of this invention ("c" stands for cyclo).

TABLE I

| Cpd. No. | $R^1$ | $R^2$ | $R^3$ | m.p. °C. |
|---|---|---|---|---|
| 1. | $C_6H_5$ | $CH_3$ | $CH_3$ | 193–194 |
| 2 | $C_6H_5$ | $C_4H_9$ | $C_4H_9$ | 120–122.5 |
| 3 | $C_6H_5$ | $c$-$C_6H_{11}$ | $c$-$C_6H_{11}$ | 173–176 |
| 4 | $C_6H_5$ | —$CH_2CH_2$—O—$CH_2$—$CH_2$— | | 165 |
| 5 | $C_6H_5$ | $CH_2C_6H_5$ | $CH_2C_6H_5$ | 202–203 |
| 6 | 4-$ClC_6H_4$ | $CH_3$ | $CH_3$ | 177–180 |
| 7 | 3-$NHCOOCH_3$—4-$CH_3C_6H_3$ | $CH_3$ | $CH_3$ | 180–185 |
| 8 | 2-$BrC_6H_4$ | —$(CH_2)_4$— | | |
| 9 | 4-$C_{12}H_{25}C_6H_4$ | —$CH_2CH_2$—S—$CH_2$— | | |
| 10 | 3-[$N(C_6H_{13})_2$]$C_6H_4$ | $CH_3$ | $C_{18}C_{37}$ | |
| 11 | 3-[$N(CH_3)_2$]$C_6H_4$ | —$CH_2CH_2$—S—$CH_2CH_2$— | | |
| 12 | 3-($NHCOOC_8H_{17}$)$C_6H_4$ | $CH_3$ | $CH_3$ | |
| 13 | 4-$COOCH_3$—$C_6H_4$ | n-$C_4H_9$ | n-$C_4H_9$ | |
| 14 | 3,4-$CH_2O_2C_6H_3$ | $C_{12}H_{25}$ | $CH_3$ | |

The compounds of this invention were evaluated as curing agents as demonstrated below. Certain abbreviations or ingredients are used in these examples, namely:

SBR 1712: oil extended (37.5 pph) styrene (23.5%)-butadiene (76.5%) copolymer, ML-4 ca. 55 at 100° C.
Cis-BR: cis-polybutadiene.
Sundex [trademark] 790 oil: aromatic oil.
Circosol [trademark] 4240 oil: aromatic oil.
AO7F: N-phenyl-N'-(1,3-dimethylbutyl-p-phenylenediamine, Flexzone [trademark] 7F, antiozonant.
MST: Mooney Scorch Time measured in minutes at temperature indicated; ASTM D1646.
$t_c90$: Time (in minutes) to obtain 90% of cure at temperature indicated; ASTM D2084).
CMT: Cure Meter Torque, 3° arc, 20 minutes; ASTM D2084.
Wax: Sunproof [trademark] improved wax, microcrystalline wax.

EXAMPLE 3

Rubber compounds were prepared on a two-roll mill using the following recipe (all in parts by weight):

| SBR 1712 | 89.4 |
|---|---|
| Cis-BR | 35.0 |
| ZnO | 3.0 |
| Stearic acid | 1.5 |
| N339 Carbon black | 75.0 |
| Sundex 790 oil | 20.0 |
| AO7F | 3.0 |
| Sulfur | 1.9 |
| Masterbatch | 226.9 |

To the masterbatch were added certain accelerators of the invention, and the compounded rubber was tested for scorching and, after curing for 10 minutes at 177° C., for physical properties.

The results are summarized in Table II.

TABLE II

| Run No. | 1 | 2 | 3 | 4 |
|---|---|---|---|---|
| Masterbatch | 226.9 | 226.9 | 226.9 | 226.9 |
| Cpd. No. 1 | 1.25 | — | — | — |
| 2 | — | 1.25 | — | — |
| 3 | — | — | 1.25 | — |
| 5 | — | — | — | 1.25 |
| MST, 135° C., min | 35.3 | 26.3 | 26.5 | 38.0 |
| $t_c90$, 177° C., min | 6.0 | 8.5 | 9.8 | 9.5 |
| 300% Modulus, mPa | 7.03 | 5.31 | 4.07 | 5.55 |
| Tensile strength, mPa | 18.41 | 17.48 | 14.07 | 17.44 |
| Elongation, % | 630 | 735 | 720 | 705 |

The data indicate that the compounds of this invention provide safe, extended scorch times while providing excellent physical properties at a practical cure rate.

EXAMPLE 4

In similar fashion as in Example 3 a compounded masterbatch was prepared using these ingredients (all in parts by weight):

| Natural rubber (SMR 5) | 100.0 |
|---|---|
| N234 Carbon Black | 50.0 |
| Circosol 4240 oil | 5.0 |
| A.O. 7F | 3.0 |
| Wax | 1.5 |
| Zinc oxide | 3.0 |
| Stearic acid | 2.5 |
| Sulfur | 2.5 |
| Masterbatch | 165 |

To 165 parts of the above masterbatch, Cpd. No. 1 (this invention), and Cpd. No. A (disclosed in U.S. Pat. No. 3,947,511) were added, respectively, and then tested. See Table III.

TABLE III

| Run No. | 5 | 6 |
|---|---|---|
| Masterbatch | 165 | 165 |
| Cpd. No. 1 | 0.6 | — |
| A | — | 0.6 |
| MST, 135° C., min | 11.0 | 9.5 |
| $t_c90$, 177° C., min | 2.7 | 2.4 |
| 300% Modulus, mPa | 11.93 | 13.17 |
| Tensile strength, mPa | 23.34 | 22.37 |
| Elongation, % | 515 | 460 |

(Compounded rubber cured for 3 minutes at 177° C.)

The data demonstrate the unexpectedly superior scorch safety, tensile strength and elongation achieved when using the compound of this invention.

EXAMPLE 5

The same masterbatch as in Example 4 was prepared to which certain accelerators were added, as indicated in Table IV. The latter also discloses the test results.

TABLE IV

| Run No. | 7 | 8 | 9 |
|---|---|---|---|
| Masterbatch | 165 | 165 | 165 |
| Cpd. No. 1 | 0.6 | — | — |
| 7 | — | 0.6 | — |
| B[(1)] | — | — | 0.6 |
| MST, 124° C., min | 29.0 | 30.0 | 46.3 |
| t$_c$90, 177° C., min | 3.0 | 3.0 | 6.6 |
| 300% Modulus, mPa | 10.6 | 9.7 | 8.4 |
| Tensile strength, mPa | 17.9 | 19.2 | 15.4 |
| Elongation, % | 455 | 510 | 500 |

Remarks:
[(1)]1,3-bis[3-(dimethylthiocarbamylthio)ureido]-4-methylbenzene, outside the invention, within the scope of U.S. Pat. No. 3,947,511.

Although compound B has an extraordinary long scorch time, it causes undesirably slow cure rate and inferior modulus and tensile strength.

EXAMPLE 6

A comparison study was undertaken between Cpd. No. 1 of this invention, prior art Cpd. No. A and a well known accelerator, N,N-oxydiethylenebenzothiazolesulfenamide (OBTS) employing the following masterbatch:

| | |
|---|---|
| SBR 1712 | 84.9 |
| Cis-BR | 35.0 |
| Zinc oxide | 3.0 |
| AO7F | 3.0 |
| N339 Carbon black | 75.0 |
| Sundex 790 oil | 20.0 |
| Stearic acid | 1.5 |
| Wax | 1.5 |
| Sulfur | 1.9 |

The compounded stock was cured for 10 minutes at 177° C. before measuring physical properties.

TABLE V

| Run No. | 10 | 11 | 12 |
|---|---|---|---|
| Masterbatch | 228.4 | 228.4 | 228.4 |
| Cpd. No.: 1 | 1.2 | — | — |
| A | — | 1.2 | — |
| OBTS | — | — | 1.2 |
| MST, 135° C., min | 36.0 | 20.0 | 27.8 |
| t$_c$90, 177° C., min | 4.3 | 3.6 | 5.8 |
| 300% Modulus, mPa | 7.9 | 8.7 | 7.6 |
| Tensile strength, mPa | 18.1 | 17.7 | 18.1 |
| Elongation, % | 615 | 540 | 625 |

The data indicate that the compound of this invention has superior scorch time over the prior art Chemical A and the commonly employed accelerator OBTS while achieving essentially the same physical properties.

EXAMPLE 7

Compound No.'s 4 and 5 were evaluated in 164.5 parts (each) of a masterbatch based on the following recipe:

| | |
|---|---|
| Natural rubber (SMR 5) | 100.0 |
| Zinc Oxide | 3.0 |
| Stearic acid | 2.0 |
| AO7F | 3.0 |
| Wax | 1.5 |
| N234 Carbon Black | 50.0 |
| Circosol 4240 oil | 5.0 |

The results are summarized in Table VI.

TABLE VI

| Run No. | 13 | 14 |
|---|---|---|
| Cpd. No.: 4 | 1.2 | — |
| 5 | — | 1.6 |
| MST, 135° C., min | 11.0 | 14.0 |
| t$_c$90, 177° C., min | 4.2 | 4.9 |
| CMT, 177° C., Mn | 3.60 | 2.67 |

As mentioned previously, the compounds of this invention may be used alone or in combination with known accelerators, however, it has been observed that such combinations unexpectedly have much faster cure rates than when either accelerator is used alone. In most cases, Mooney scorch time is also reduced indicating extraordinarily fast curing conditions.

EXAMPLE 8

Using the masterbatch of Example 6, the following experiments were carried under the conditions of said Example. For results see Table VII.

TABLE VII

| Run No. | 15 | 16 | 17 |
|---|---|---|---|
| Masterbatch | 228.4 | 228.4 | 228.4 |
| OBTS | 1.2 | — | 0.5 |
| Cpd. No. 1 | — | 1.2 | 1.0 |
| MST, 124° C., min | 27.8 | 36.0 | 26.3 |
| t$_c$90, 177° C., min | 5.8 | 4.3 | 4.0 |
| 300% Modulus, mPa | 7.5 | 7.9 | 9.4 |
| Tensile strength, mPa | 18.1 | 18.1 | 17.6 |
| Elongation, % | 625 | 615 | 530 |

EXAMPLE 9

Employing the masterbatch and procedure of Example 7, Runs No. 18, 19 and 20 were undertaken with the results indicated in Table VIII.

TABLE VII

| Run No. | 18 | 19 | 20 |
|---|---|---|---|
| Masterbatch | 164.5 | 164.5 | 164.5 |
| OBTS | 0.9 | — | 0.45 |
| Cpd. No. 1 | — | 1.2 | 0.45 |
| MST, 135° C., min | 11.0 | 11.0 | 11.8 |
| t$_c$90, 177° C., min | 4.3 | 4.2 | 3.7 |

The results demonstrate the exceptionally fast cure rate of tire combination of the known sulfenamide accelerator and a compound of this invention.

Also, when using mixtures of the instant compounds with known accelerators similar results are observed regarding especially fast cure rate and/or scorch time when maintaining a CI/KA weight ratio of 4/1–1/3, preferably 2/1–1/2 and most preferably 2/1–1/1, wherein CI stands for "compounds of this invention" and KA means "known curing accelerator."

Suitable benzothiazole sulfenamide accelerators for use with the instant chemicals include N,N-diethyl-2-benzothiazole sulfenamide, N,N-dicyclohexyl-2-benzothiazole sulfenamide, N-oxydiethylene-2-benzothiazole sulfenamide, N-tert-butyl-2-benzothiazole sulfenamide, N-cyclohexyl-2-benzothiazole sulfenamide, 2-(4-morpholino)dithiobenzothiazole sulfenamide.

Thiurams which may be used with the compounds of this invention include tetramethylthiuram monosulfide, tetramethylthiuram disulfide, dipentamethylenethiuram disulfide, dipentamethylenethiuram tetrasulfide, dipentamethylenethiuram monosulfide, tetrabutylthiuram disulfide, tetrabutylthiuram monosulfide, tetraethylthiuram monosulfide, tetraethylthiuram disulfide, and the like.

Certain mono-isocyanates are useful as intermediates for making the corresponding compounds wherein $R^1$ is phenyl substituted with, among other things, $NHCOOR^7$. Such mono-isocyanates have the formula $R^*NHC(O)NHSC(S)NR^2R^3$, wherein $R^2$ and $R^3$ have the above meanings and $R^*$ is phenyl or $C_7-C_9$ alkylphenyl substituted with an NCO group. Such compounds may also be used as rubber curatives.

I claim:

1. A curable rubber composition comprising:
   (a) an accelerator compound of the formula $$R^1\text{—}NHC(O)NHSC(S)NR^2R^3$$

wherein $R^1$ is phenyl; and $R^2$ and $R^3$ are methyl; and
   (b) at least one member of the group consisting of uncured natural rubber, cis-polyisoprene, trans-polyisoprene, polybutadiene, styrene-butadiene copolymer, acrylonitrile-butadiene copolymer and ethylene-propylene-nonconjugated diene terpolymer.

* * * * *

UNITED STATES PATENT AND TRADEMARK OFFICE
CERTIFICATE OF CORRECTION

PATENT NO. : 4,631,316

DATED : December 23, 1986

INVENTOR(S) : Joseph F. Stieber

It is certified that error appears in the above-identified patent and that said Letters Patent is hereby corrected as shown below:

In Column 1, line 21 "A compound" should read

-- Compound A, --

Signed and Sealed this

First Day of November, 1988

*Attest:*

DONALD J. QUIGG

*Attesting Officer*   *Commissioner of Patents and Trademarks*